United States Patent
Barra et al.

(10) Patent No.: US 6,310,176 B1
(45) Date of Patent: Oct. 30, 2001

(54) ANTIMICROBIALLY ACTIVE POLYPEPTIDES

(75) Inventors: Donatella Barra; Maurizio Simmaco, both of Rome (IT)

(73) Assignee: SBL Vaccin AB, Stockholm (SE)

( * ) Notice: Subject to any disclaimer, the term of this patent is extended or adjusted under 35 U.S.C. 154(b) by 0 days.

(21) Appl. No.: 09/319,730

(22) PCT Filed: Dec. 12, 1997

(86) PCT No.: PCT/SE97/02075

§ 371 Date: Aug. 24, 1999

§ 102(e) Date: Aug. 24, 1999

(87) PCT Pub. No.: WO98/25961

PCT Pub. Date: Jun. 18, 1998

(30) Foreign Application Priority Data

Dec. 13, 1996 (SE) .................................. 9604593

(51) Int. Cl.[7] ................... C07K 5/00; C07K 7/00; A61K 38/00; A61K 37/02
(52) U.S. Cl. ................... 530/300; 530/300; 530/324; 530/325; 530/350; 530/326; 514/2; 514/12; 525/54.1; 536/23.2
(58) Field of Search .................. 435/6; 525/54.1; 530/300, 324; 514/16, 12, 13; 536/23.2

(56) References Cited

U.S. PATENT DOCUMENTS 5,447,914 * 9/1995 Travis et al. ......................... 514/16

FOREIGN PATENT DOCUMENTS

WO95/27728 10/1995 (WO).

OTHER PUBLICATIONS

Sequence Database Printout.*
Simmaco et al., "Temporins, antimicrobial peptides from the European red frog *Rana temporaria*", European Journal of Biochemistry, vol. 242, pp. 788–792.*

"Temporins, antimicrobial peptides from the European red frog *Rana temporaria*", Maurizio Simmaco et al., *Eur. J. Biochem.*, vol. 242 (1996) pp. 788–792.

"Amphibian skin: a promising resource for antimicrobial peptides", Donnatella Barra et al., *TibTech*, vol. 13 (Jun. 1995) pp. 205–209.

"Antimicrobial Peptides from Skin Secretions of *Rana esculenta*", Maurizio Simmaco et al., *The Journal of Biological Chemistry*, vol. 269, No. 16, (Apr. 22, 1994) pp. 11956–11961.

"Brevinin–1 and –2, Unique Antimicrobial Peptides from the Skin of the Frog, *Rana Brevipoda Porsa*", Noriyuki Morikawa et al., *Biochemical and Biophysical Research Communications*, vol. 189, No. 1 (Nov. 30, 1992) pp. 184–190.

"Isolation and Characterization of Novel Antimicrobial Peptides, Rugosins A, B and C, from Skin of the Frog, *Rana rugosa*", Shintaro Suzuki et al., *Biochemical and Biophysical Research Communications*, vol. 212, No. 1 (Jul. 6, 1995) pp. 249–254.

"Ranalexin: A Novel Antimicrobial Peptide from Bullfrog (*Rana catesbeiana*) Skin, Structurally Related to the Bacterial Antibiotic, Polymyxin", Douglas P. Clark et al., *The Journal of Biological Chemistry*, vol. 269, No. 14 (Apr. 8, 1994) pp. 10849–10855.

"Antimicrobial Peptides from the Skin of a Korean Frog, *Rana rugosa*", Jin Mo Park et al., *Biochemical and Biophysical Research Communications*, vol. 205, No. 1 (Nov. 30, 1994) pp. 948–954.

* cited by examiner

*Primary Examiner*—Karen Cochrane Carlson
*Assistant Examiner*—Patricia Robinson
(74) *Attorney, Agent, or Firm*—Burns, Doane, Swecker & Mathis, L.L.P.

(57) ABSTRACT

A polypeptide selected from peptides (1) and functional derivatives and pharmaceutically acceptable salts thereof; pharmaceutical compositions containing one or more of these polypeptides; and a method for inhibiting microbial growth in animals using such polypeptides.

17 Claims, 1 Drawing Sheet

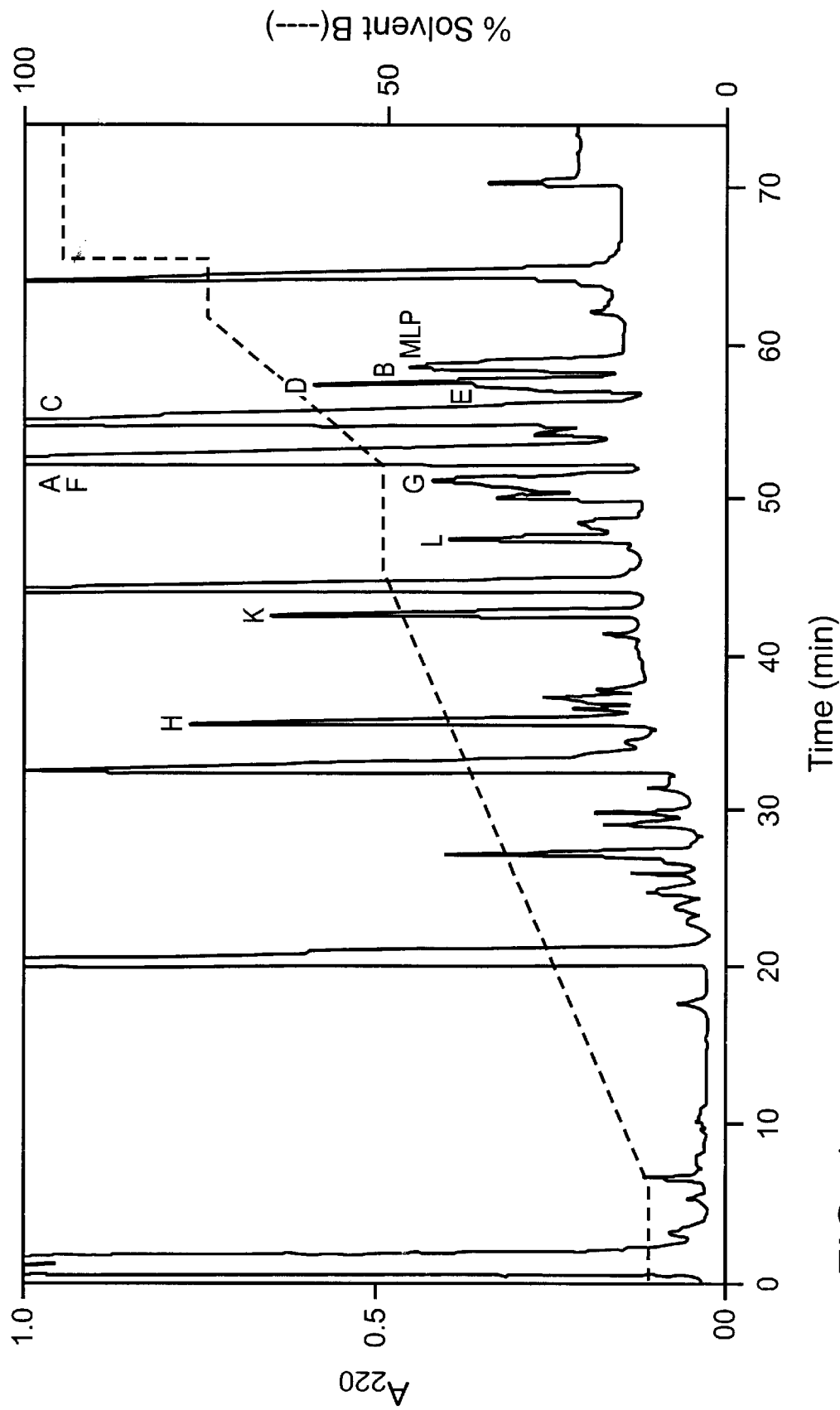
FIG. 1 Reverse-phase HPLC of skin secretion of R. temporaria. The elution position of the peptides reported in Table 1 is indicated by the corresponding letters. For details, see the Materials and Methods section.

ANTIMICROBIALLY ACTIVE POLYPEPTIDES

The present invention relates to new polypeptides for therapeutic use and their functional derivatives and pharmaceutically acceptable salts. The new polypeptides have each per se or in combination of one or more of the peptides anti-bacterial or fungal use.

Skin secretions of frogs contain many different types of antibacterial peptides (Barra, D. & Simmaco, M. (1995) Amphibian skin: a promising resource for antimicrobial peptides, Trends Biotechnol. 13, 205–209 for a recent review). In particular, a variety of such peptides has been isolated from several Rana species. They all contain two cysteine residues close to the COOH-terminus which form an intramolecular disulfide bridge. Four different groups of these peptides can be discerned. One is the brevinin 1 family, which includes brevinin 1 from *Rana brevipoda porsa* (Morikawa, N., Hagiwara, K. & Nakajima, T. (1992) Brevinin-1 and Brevinin-2, unique antimicrobial peptides from the skin of the frog, *Rana brevipoda porsa*, Biochem. Biophys. Res. Commun. 189, 184–190), brevinin 1E from *Rana esculenta* (Simmaco, M., Mignogna, G., Barra, D. & Bossa, F. (1994) Antimicrobial peptides from skin secretion of *Rana esculenta*. Molecular cloning of cDNA encoding esculentin and isolation of new active peptides, J. Biol. Chem. 269, 11956–11961), ranalexin from *Rana catesbeiana* (Clark, D. P., Durell, S., Maloy, W. L. & Zasloff, M. (1994) Ranalexin, a novel antimicrobial peptide from bullfrog (*Rana catesbeiana*) skin, structurally related to the bacterial antibiotic, polymixin, J. Biol. Chem. 269, 10849–10855) and gaegurin 5 and 6 from *Rana rugosa* (Park, J. M., Jung, J.-E. & Lee, B. J. (1994) Antimicrobial peptides from the skin of a korean frog, *Rana rugosa*, Biochem. Biophys. Res. Commun. 205, 948–954). These peptides are composed of 20–24 amino acid residues. In addition to their antibacterial action, brevinin. 1E and ranalexin also have high hemolytic activity. A second group are the brevinin 2 peptides, which contain 29–34 amino acids. Besides brevinin 2 from *R. brevipoda porsa* (Morikawa, N., Hagiwara, K. & Nakajima, T. (1992) Brevinin-1 and Brevinin-2, unique antimicrobial peptides from the skin of the frog, *Rana brevipoda porsa*, Biochem. Biophys. Res. Commun. 189, 184–190), several peptides from *R. esculenta* (Simmaco, M., Mignogna, G., Barra, D. & Bossa, F. (1994) Antimicrobial peptides from skin secretion of *Rana esculenta*. Molecular cloning of cDNA encoding esculentin and isolation of new active peptides, J. Biol. Chem. 269, 11956–11961), the gaegurins 1–3 (Park, J. M., Jung, J.-E. & Lee, B. J. (1994) Antimicrobial peptides from the skin of a korean frog, *Rana rugosa*, Biochem. Biophys. Res. Commun. 205, 948–954) and rugosins A and B from *R. rugosa* (Suzuki, S., Ohe, Y., Okubo, T., Kakegawa, T. & Tatemoto, K. (1995) Isolation and characterization of novel antimicrobial peptides, rugosin A, B and C, from the skin of the frog, *Rana rugosa*, Biochem. Biophys. Res. Commun. 212, 249–254) belong to this family. A third group are the 37 residue peptides esculentin 2 from *R. esculenta* (Simmaco, M., Mignogna, G., Barra, D. & Bossa, F. (1994) Antimicrobial peptides from skin secretion of Rana esculenta. Molecular cloning of cDNA encoding esculentin and isolation of new active peptides, J. Biol. Chem. 269, 11956–11961) and gaegurin 4 (Park, J. M., Jung, J.-E. & Lee, B. J. (1994) Antimicrobial peptides from the skin of a korean frog, *Rana rugosa*, Biochem. Biophys. Res. Commun. 205, 948–954) and rugosin C from *R. rugosa* (Suzuki, S., Ohe, Y., Okubo, T., Kakegawa, T. & Tatemoto, K. (1995) Isolation and characterization or novel antimicrobial peptides, rugosin A, B and C, from the skin of the frog, *Rana rugosa*, Biochem. Biophys. Res. Commun. 212, 249–254). Lastly, esculentin 1 from skin secretion of *R. esculenta* (Simmaco, M., Mignogna, G., Barra, D. & Bossa, F. (1994) Antimicrobial peptides from skin secretion of *Rana esculenta*. Molecular cloning of cDNA encoding esculentin and isolation of new active peptides, J. Biol. Chem. 269, 11956–11961), a 46 amino acid peptide that has the highest antibacterial activity of all the Rana peptides characterized so far. In addition, it is also active against *Candida albicans, Saccharomyces cerevisiae* and *Pseudomonas aeruginosa*.

The present invention has for an object to provide relatively small polypeptides of antimicrobial activity.

Another object of the invention is to provide such new polypeptides having antibacterial or fungal use.

Yet another object of the invention is to provide pharmaceutical compositions containing one or more such polypeptides contained in a pharmaceutically acceptable matrix.

Still another object of the invention is to provide a method for inhibiting microbial growth in animals, such as mammals including man.

For these and other objects which will be clear from the following disclosure the invention provides for the following new peptides [SEQ ID NOS: 1–11]:

F L P L I G R V L S G I L - amide
L L P I V G N L L K S L L amide
L L P I L G N L L N G L L - amide
L L P I V G N L L N S L L - amide
V L P I I G N L L N S L L - amide
F L P L I G K V L S G I L - amide
F F P V I G R I L N G I L - amide
L S P N L L K S L L - amide
L L P N L L K S L L - amide
F V Q W F S K F L G R I L - amide
G L L S G L K K V G K H V A K N V A V S L M D S L K C K I S G D C Particularly preferred polypeptides [SEQ ID NOS: 1, 2, 6, 7, and 10] are the following:

F L P L I G R V L S G I L - amide
L L P I V G N L L K S L L - amide
F L P L I G K V L S G I L - amide
F F P V I G R I L N G I L - amide
F V Q W F S K F L G R I L - amide Within the scope of the invention there are also included functional derivatives and pharmaceutically acceptable salts of the polypeptides mentioned above.

The polypeptides according to the present invention can be used each per se or can be used in combinations of two or more polypeptides.

The polypeptides are therapeutically useful, such as for antimicrobial use, including antibacterial or fungal use.

The invention also provides for the use of one or more of the polypeptides disclosed above for the manufacture of a medicament having antimicrobial activity.

Furthermore, the invention provides for a pharmaceutical composition containing as an active ingredient one or more polypeptides as described above in an effective amount together with a pharmaceutically acceptable carrier or diluent. Said carrier or diluent is suitably adapted for oral, intraveneous, intramuscular or subcutaneous administration.

According to the invention there is also provided a cDNA clone having the sequence selected from the sequences shown as clone Rt-5, Rt-6 and Rt-17 as disclosed in the following.

Finally, the invention provides for a method for inhibiting microbial growth in animals, such as mammals including man, comprising the step of administering to an animal subject to a disorder caused by antimicrobial attack one or more polypeptides as described above or a composition thereof, an inhibitory amount being administered.

Such method can be directed to intestinal use constituted by oral administration of a composition as defined above in a slow release form. The method can also be directed to administration by injection of such a composition in an injectable dose form.

With regard to the expression "functional derivatives thereof" it is well known in regard to the technical area to which the present invention pertains that minor amino acid substitutions can be made to the polypeptide which do not affect or do not substantially affect the function of the polypeptide. Determination of conceivable substitutions is accomplished according to procedures well known to those skilled in the art. Thus, all polypeptides having substantially the same amino acid sequence, substantially the same helical structure and substantially the same biological activity, such as antimicrobial and lytic activity, are within the scope of this invention.

Also within the scope of the present invention are pharmaceutically acceptable salts of the polypeptides of this invention. Such salts are formed by methods well known to skilled artisans. Thus, for example base salts of the polypeptides can be prepared according to conventional methods. When in the instant disclosure including the claims the term polypeptide is used said term is intended to include both functional derivatives and pharmaceutically acceptable salts of the polypeptides.

The active polypeptide according to the present invention can be formulated for use in human or veterinary medicine for therapeutic or prophylactic use. The active preparations are normally administered orally, rectally or parenterally, such as by injection in the form of a pharmaceutical preparation or composition comprising the active constituents in combination with a pharmaceutically acceptable carrier which may be solid, semi-solid or liquid, or contained in a capsule, such as when orally administered. The administration may also take the form of topical application. As examples of pharmaceutical preparations there may be mentioned tablets, drops, solutions and suppositories. Usually, the active constituent constitutes the minor part of the preparation, such as from about 0.1 to about 50% thereof based on weight.

In order to prepare pharmaceutical compositions in the form of dose units for oral application the polypeptide of the invention can be mixed with a solid, pulverulent or other carrier, for example lactose, saccharose, sorbitol, mannitol, starch, such as potatoe starch, corn starch, millopectine, cellulose derivative or gelatine, and may also include lubricants, such as magnesium or calciun stearate, or polyethylene glycol waxes compressed to the formation of tablets or bodies for dragées. The dose units slay also be presented in a coated form of enteric type.

By using several layers of the carrier or diluent tablets operating with slow release can be prepared.

Liquid preparations for oral application or for injection can be made in the form of elexirs, syrups or suspensions, for example solutions containing from 0.1 to 20% by weight of active substance, sugar and a mixture of ethanol, water, glycerol, propyleneglycol and possibly other additives of a conventional nature.

The dose by which the active constituent is administered may vary within wide limits and is dependent on different factors, such as the seriousness of the disorder, the age and the weight of the patient and can be adjusted individually.

In finding the new polypeptides according to the present invention the skin of *Rana temporaria*, a red frog found in many parts of Central Europe, was used. A cDNA library prepared from the skin of this frog was screened with a DNA fragment encoding the signal peptide of the precursor of esulentin 1 from *R. esculenta*. Using this approach several clones could be isolated with inserts that potentially coded for the precursors of new peptides. The new peptides which could be isolated from skin secretion of *R. temporaria* were termed temporins and were found to have biological activities, such as antibacterial activity, both each per se and in synergistic combinations.

The present invention will now be described by non-limiting examples through the following disclosure. This disclosure is made with reference to the appended drawings, wherein:

FIG. 1 shows the nucleotide sequences of 3 clones and inserts present therein and also deduced amino acid sequences; and FIG. 2 shows a diagram on reverse-phase HPLC of skin secretion or *R. temporaria*.

MATERIALS AND METHODS

Enzymes and Reagents. Analytical grade chemicals were from Merck, HPLC-grade solvents from Carlo Erba, sequenal-grade chemicals from Perkin Elmer. Media for antimicrobial assays were from Difco, agarose (A6013) from Sigma. Restriction enzymes and DNA modifying enzymes were from Boehringer Mannheim, deoxyribonucleotides from Pharmacia. DNA sequences were determined with a "Sequenase kit" (version2.0, U.S. Biochemicals) using [a-$^{35}$S]dATP. Synthetic peptides were purchased from TANA laboratories (Huston, USA).

Isolation of RNA and cloning procedure. For these studies the skin of two specimens of *R. temporaria* was used. The isolation of poly(A)-rich RNA by affinity chromatography over oligo(dT)-cellulose and the preparation of the cDNA library were performed according to Richter et al., (1990b). (Richter, K., Egger, R. & Kreil, G. (1990b) Molecular cloning of a cDNA encoding the bombesin precursor in skin of *Bombina variegata*, FEBS Lett. 262, 353–355.)

A cDNA library comprising about 10,000 clones was screened with a 240 bp fragment obtained by digestion of the esculentin 1 cDNA with HindIII (Simmaco, M., Mignogna, G., Barra, D. & Bossa, F. (1994) Antimicrobial peptides from skin secretion of *Rana esculenta*. Molecular cloning of cDNA encoding esculentin and isolation of new active peptides. J. Biol. Chem. 269, 11956–11961). This fragments encodes the prepro-region of the esculentin 1 precursor. The probe was labelled by random priming (Boehringer Mannheim). Hybridization was performed at 55° C. for 16 h in 100 mM sodium phosphate buffer, pH 7.2, containing 850 mM NaCl, 1 mM EDTA, 10× Denhardt's solution, 0.1% SDS and 100 mg/ml yeast tRNA. Filter papers (Whatman 541, 11 cm×11 cm) were washed twice for 15 min at 50° C. wih SSPE (0.3 M NaCl, 20 mM sodium phosphate, pH 7.4, 2 mM EDTA), 0.2% SDS. Positive clones were selected and analysed by cleavage with restriction enzymes and nucleotide sequencing.

Northern blot analysis. Poly(A)-rich RNA (5 mg) was fractionated by electrophoresis in 1.2% agarose gels containing 0.8 M formaldehyde (Arrand, J. E. (1985) Preparation of nucleic acid probes, in Nucleic acid hybridization: a practical approach (Hames, B. D. & Higgins, S. J., eds) pp 17–45, IRL Press, Oxford) and blotted directly onto Nytran sheets (Schleicher & Schuell). The insert of clone Rt-17 was labeled by random priming and used for probing the Northern blot. Filters were washed at 55° C. in 0.1×SSPE, 0.1% SDS, and then used for autoradiography.

Collection and purification of skin secretions. Three specimens of *R. temporaria* (30–35 g each) were captured near Salzburg (Austria). They were maintained in a terrarium in our laboratory for 1 year and feed larvae of *Tenebrio molitor*. Skin secretions were collected at intervals of three weeks by a mild electrical shock (12 V, feet to head). The secretion was collected from the surface of a single frog by washing its dorsal region with 10 ml 0.05% (by vol.) acetic acid. The secretions of the three frogs were combined and lyophilized. Suitable aliquots were fractionated by HPLC on a Beckman model 332 system using a reverse-phase column (Aquapore RP-300, 7 mm×250 mm. Applied Biosystems) eluted with a gradient of 10–70% acetonitrile/isopropanol (4.1) in 0.2% (by vol.) trifluoroacetic acid, at a flow rate of 1.8 ml/min. Elution of the peptides was monitored on a Beckman 165 spectrophotometer at 220 nm. Peak fractions were collected and lyophilized. A small aliquot of each peak was subjected to N-terminal analysis following derivatization with dansyl chloride and reverse phase HPLC separation (Simmaco, M., De Biase, D., Barra, D. & Bossa, F. (1990b) Automated amino acid analysis and determination of amidated residues using pre-column derivatization with dansyl-chloride and reverse-phase high performance liquid chromatography, J. Chromatogr. 504, 129–138). Further purification of peptides was achieved using a macroporous $C_{18}$ column (4.6 mm×150 mm, Supelco) developed with an appropriately modified gradient of the same solvent system as described above.

Structural analysis. Amino acid analyses were performed with a Beckman System Gold analyzer, equipped with an ion-exchange column and ninhydrin derivatization, after vapor phase hydrolysis of the peptides (1–2 nmol) in 6 N HCl for 24 h. Peptide sequences were determined by automated Edman degradation with a Perkin-Elmer model AB476A sequencer. In some cases, information on the amidation state of the C-terminus was confirmed by mass spectral analysis and/or carboxypeptidase Y digestion (Simmaco, M., De Biase, D., Barra, D. & Bossa, F. (1990b) Automated amino acid analysis and determination of amidated residues using pre-column derivatization with dansyl-chloride and reverse-phase high performance liquid chromatography, J. Chromatogr. 504, 129–138).

Antimicrobial assay. The antibacterial activity was tested against *Bacillus megaterium* BM11, *Staphylococcus aureus* Cowahl, Streptococcus pyogenes b hemolytic group A, *Pseudomonas aeruginosa* ATCC 15692, *Escherichia coli* D21, *E. coli* D21e7, *E. coli* D21f1, *E. coli* D21f2 and *E. coli* D22, using an inhibition zone assay on LB broth/1% agarose plates seeded with 2×10⁵ viable bacteria (Hultmark, D., Engström, Å., Andersson, K., Steiner, H., Bennich, H. & Boman, H. G. (1983) Insect immunity. Attacin, a family of antibacterial proteins from *Hyulophora cecropin*, EMBO J. 2, 571–576). Fresh cultures of *Candida albicans* ATCC 10261 were inoculated in WB broth, pH 6.5, and grown at 37° C. to approximately 0.6 $OD_{600}$. Before plating, cultures were diluted 300 fold and then incubated overnight at 37° C. in the presence of the test peptide, the concentration of which was established by amino acid analysis. Inhibition zones were measured and the lethal concentration (LC, the lowest concentration that inhibits the growth) was calculated from the diameter of the zones obtained in serial dilutions of the test substance by using the formula given in Hultmark, D., Engström, Å., Andersson, K., Steiner, H., Bennich, H. & Boman, H. G. (1983) Insect immunity. Attacin, a family of antibacterial proteins from *Hyulophora cecropin*, EMBO J. 2, 571–576). Values are expressed as the mean of at least 5 experiments with a divergence of not more than one dilution step.

Circular dichroism measurements. CD measurements were carried out on a Jasco J710 spectropolarimeter, equipped with a DP 520 processor, at 20° C., using a quartz cell of 2 mm pathlength. CD spectra were the average of a series of 3 scans. Ellipticity is reported as the mean molar residue ellipticity (q), expressed in deg $cm^2 dmol^{-1}$. Peptide concentrations were determined by amino acid analysis.

RESULTS

Analysis of cDNA clones encoding the precursors. A 240 bp HindIII fragment encoding the signal peptide and the propart of the esculentin 1 precursor was used as a probe to screen the cDNA library prepared from skin of *R. temporaria*. Six positive clones were detected. The sequences of the inserts present in clones Rt-5, Rt-6 and Rt-17 are shown in FIG. 1. Excluding the poly(A) tail, these cDNAs comprise 323, 356 and 329 nucleotides, respectively. After the first methionine codon, they contain open reading frames which can be translated into polypeptides containing 58 (Rt-6) or 61 amino acids (Rt-5 and Rt-17). The deduced sequences all have the typical features of peptide precursors. They start with a signal peptide containing a cluster of hydrophobic residues. The cleavage site for signal peptidase is most likely located after the cysteine residue at position 22 (von Heine, G. (1983) Patterns of amino acids near signal-sequence cleavage sites, Eur. J. Biochem. 133, 17–21). The sequences of the putative mature peptides are preceded by a Lys-Arg, a typical processing site for prohormone convertases. All these precursors polyptpeides terminate with the sequence Gly-Lys. Hydrolysis by carboxypeptidase E would expose a C-terminal glycine which is required for the formation of COOH-terminal amides. The predicted end products would be amidated peptides containing 13 amino acids for clones Rt-5 and Rt-17, while Rt-6 has a 9 bp deletion in this region, thus codes only for a decapeptide.

Northern blot analysis. In poly(A)-rich RNA from skin of *R. temporaria*, the probe derived from clone Rt-17 recognized an abundant message, detected as a single, rather broad band in the range of 400–500 nucleotides. Under the same conditions, no signal could be obtained from the skin of other amphibian species such as *R. esculenta, Xenopus laevis* and *Bufo viridis*.

Isolation and analysis of peptides from skin secretion. After electrical stimulation of 3 specimens of *R. temporaria*, about 20 mg of lyophilized material could be obtained. After a preliminary HPLC purification (FIG. 2), each fraction was subjected to N-terminal analysis, in order to identify those with amino-terminal Leu or Phe as predicted from the cDNA sequences. The relevant fractions were further purified by HPLC and subjected to amino acid and sequence analysis. Following this approach, the three predicted peptides were found to be indeed present in the secretion. Other molecules, structurally related to these peptides, were also isolated. The sequences of these peptides, which are termed temporins, are shown in Table 1. In this Table the amount of each peptide recovered from the secretion is also included. Along the HPLC profile reported in FIG. 2, the elution position of the various peptides is indicated. The structure of temporin E, with Val at its N-terminus, and which coeluted in part with temporin D, is also shown in the Table. Temporins are all amidated at their C-terminus, as predicted from the structure of the precursors (see above), and contain a prevalence of hydrophobic amino acids. Each of these peptides contains 13 residues, with the exception of temporins H and K, which are 10 residue long. Except for temporins C, D, and E, all of these peptides have at least one basic residue (either Lys or Arg). In the course of this analysis, a 22-residue peptide was also found in the skin secretion (see Table 1). Its sequence shows some similarity with that of melittin, a hemolytic peptide from bee venom (Habermann, E. (1972) Bee and wasp venoms, Science 251, 1481–1485). It was thus named melittin-like peptide (MLP).

Assays for biological activity. The antimicrobial activity of the purified temporins was first tested against *B. mega-* terium and E. coli D21. Temporins A, B, F, G and L were active on both bacterial strains, whereas temporins C, D, E, H and K only showed some activity against B. megaterium, the most sensitive bacterium.

The recovery of some of the temporins was too low to allow a detailed characterization of their biological properties. To confirm the structure and in order to obtain more material temporins A, B, D and H were chemically synthesized. The antimicrobial activity of synthetic temporins A and B, expressed as lethal concentration values, is reported in Table 2, together with the results obtained on red blood cell lysis. As references are included esulentin 1 from R. esculenta (Simmaco, M., Mignogna, G., Barra, D. & Bossa, F. (1994) Antimicrobial peptides from skin secretion of Rana esculenta. Molecular cloning of cDNA encoding esculentin and isolation of new active peptides, J. Biol. Chem. 269, 11956–11961), cecropin from insect hemolymph (Steiner, H., Hultmark, D., Engström, Å, Bennich, H. & Boman, H. G. (1981) Sequence and specificity of two antibacterial proteins involved in insect immunity, Nature 292, 246–248) and melittin from honeybee venom (Habermann, E. (1972) Bee and wasp venoms, Science 251, 1481–1485).

Synthetic temporins A and B showed the same activities as their natural counterparts while temporins D and H were found to be without any biological activity of their own or as enhancers of other Rana peptides. Temporin A is about three times more active than temporin B against S. aureus and S. pyogenes. On the other hand, these two temporins were poorly active against E. coli D21 and completely inactive against P. aeruginosa. This indicates that temporins A and B act specifically against gram-positive bacteria.

Linear sulfur free antibacterial peptides like cecropins are inactive against fungi while the defensins (with three S—S bridges) show antifungal activity. Temporins A and B are active against C. albicans, and their potency is of the same order as reported for dermaseptin from the South American frog Phyllomedusa sauvagei (Mor, A., Hani, K. & Nicolas, P. (1994) The vertebrate peptide antibiotics dermaseptins have overlapping structural features but target specific microorganisms, J. Biol. Chem. 269, 31635–61641).

The antibacterial activity of temporins A and B was also tested against three strains of E. coli D21, D21e7, D21f1 and D21f2, with consecutive mutations deleting increasing amounts of the side chain in LPS (Boman, H. G. & Monner, D. A. (1975) Characterization of lipopolysaccharides from Escherichia coli K12 mutants, J. Bacteriol. 121, 455–464). Strain D22 has a permeable outer membrane due to a mutation in the envA gene (Normark, S., Boman, H. G. & Matsson E. (1969), Mutant of Escherichia coli with anomalous cell division and ability to decrease episomally and chromosomally mediated resistance to ampicillin and several antibiotics. J. Bacteriol, 97, 1334–1342). The activities of the temporins were tested in the absence or in the presence of the basal medium E (Vogel, H. J. & Bonner, D. M. (1956) Acetylornithinase of Escherichia coli: partial purification and some properties, J. Biol. Chem. 218, 97–106), The results in Table 3 show medium E was found to increase the activity of tempors in all strains tested. However no similar effects were seen with gram positive bacteria. CD spectra showed that the increase in activity was correlated to an increased helix formation as found before for FALL-39 (Ageberth, G., Gunne, H., Odeberg, J., Kogner, P., Boman, H. G. & Gudmundsson, G. H. (1995) FALL-39, a putative human peptide antibiotic, is cysteine-free and expressed in bone marrow and testis, Proc. Natl. Acad. Sci. USA 92, 195–199).

Within the term "functional derivatives" used herein are included the peptides with free carboxyl groups and also acid addition salts. Therefore the invention is not restricted to the specific peptides disclosed.

TABLE 1

Sequences of Rana temporaria skin peptides and relative amount in the secretion. Peptides [SEQ ID NOS: 1–13] for which the structure of the corresponding precursor has been predicted from cDNAs are marked with the asterisk. a indicates an amidated COOH-terminus. MLP, melittin-like peptide. Identical residues are boldfaced. Gaps (-) were inserted to maximize identities.

| Peptide | Sequence | Yield nmol/mg |
|---|---|---|
| Temporin A | FLPLIGRVLSGILa | 14.5 |
| Temporin B* | LLPIVGNLLKSLLa | 19.4 |
| Temporin C | LLPILGNLLNGLLa | 37.5 |
| Temporin D | LLPIVGNLLNSLLa | 1.1 |
| Temporin E | VLPIIGNLLNSLLa | 1.2 |
| Temporin F | FLPLIGKVLSGILa | 13.5 |
| Temporin G* | FFPVIGRILNGILa | 16.8 |
| Temporin H* | LSP---NLLKSLLa | 8.7 |
| Temporin K | LLP---NLLKSLLa | 9.8 |
| Temporin L | FVQWFSKFLGRILa | 3.6 |
| MLP | FIGSALKVLAGVLPSVISWVK---Qa | 5.1 |
| Melittin | GIGAVLKVLTTGLPALISWIKRKRQQa | |

TABLE 2

Antimicrobial and lytic activity of Rana temporaria peptides. Lethal concentrations were calculated from inhibition zones on agarose plates seeded with the respective organisms. The data for cecropin are from Hultmark et al. (1983). S. Pyogenes β hem. group A and Ps. aeruginosa ATCC15692 are clinical isolates kindly provided by Dr. Paolo Visca, Institute of Microbiology, University of Rome La Sapienza. NT, not tested.

| | Lethal concentration of | | | | | |
|---|---|---|---|---|---|---|
| Organism and strain | Temporin A µM | Temporin B | Esculentin 1 | Cecropin A | MLP | Melittin |
| B. megaterium BmII | 1.2 | 2.8 | 0.1 | 0.5 | NT | 0.6 |
| S. aureus Cowan1 | 2.3 | 6.0 | 0.4 | >200 | NT | 0.2 |
| Y. pseudotubercolosis | 7.0 | 7.0 | NT | 0.5 | NT | NT |

TABLE 2-continued

Antimicrobial and lytic activity of Rana temporaria peptides. Lethal concentrations were calculated from inhibition zones on agarose plates seeded with the respective organisms. The data for cecropin are from Hultmark et al. (1983). *S. Pyogenes* β hem. group A and *Ps. aeruginosa* ATCC15692 are clinical isolates kindly provided by Dr. Paolo Visca, Institute of Microbiology, University of Rome La Sapienza. NT, not tested.

|  | Lethal concentration of | | | | | |
|---|---|---|---|---|---|---|
| Organism and strain | Temporin A $\mu M$ | Temporin B | Esculentin 1 | Cecropin A | MLP | Melittin |
| *S. pyrogenes* βhem. group A | 2.0 | 7.0 | NT | NT | NT | NT |
| *E. coli* D21 | 11.9 | 21.0 | 0.2 | 0.3 | NT | 0.8 |
| *Ps. aeruginosa* ATCC15692 | >360 | >360 | 0.7 | NT | NT | NT |
| *C. albicans* | 3.4 | 4.0 | 0.5 | NT | NT | NT |
| Human red cells | >120 | >120 | >200 | >400 | 0.5 | 0.9 |

TABLE 3

Antibacterial activity of temeporins A and B against *E. coli* D21 and related LPS modified strains. Assays were performed in LB broth/1% agarose, in the absence or in the presence of medium E (Vogel & Bonner 1956). Bacterial strains were kindly provided by Prof. H. G. Boman, University of Stockholm

|  | Lethal concentration for | | | | |
|---|---|---|---|---|---|
| Compound | D21 $\mu M$ | D21e7 | D21f1 | D21f2 | D22 |
| Temporin A | 11.9 | 1.4 | 0.9 | 4.8 | 3.4 |
| Temporin A + medium E | 5.3 | 1.4 | 3.0 | 2.0 | 0.4 |
| Temporin B | 21.0 | 13.2 | 10.0 | 3.3 | 11.2 |
| Temporin B + medium E | 3.4 | 4.2 | 3.5 | 9.3 | 12.2 |

SEQUENCE LIST

[SEQ ID NOS:14—17]

Clone Rt-5

```
1   ACAATTCTGAGCCAACTGAACCACCCGAGCCCAAAGATGTTCACCTTGAAGAAATCCCTG
                                          M  F  T  L  K  K  S  L

61  TTACTCCTCTTTTTCCTTGGGACCATCAACTTATCTCTCTGTGAGGAAGAGAGAAATGCA
    L  L  L  F  F  L  G  T  I  N  L  S  L  C  E  E  E  R  N  A

121 GAAGAAGAAAGAAGAGATGAACCAGATGAAAGGGATGTTCAAGTGGAAAAACGACTTTTA
    E  E  E  R  R  D  E  P  D  E  R  D  V  Q  V  E  K  R  L  L

181 CCAATTGTTGGAAACCTGCTCAAGAGCTTGTTGGGAAAATAACCAAAAATGTTAAGAATG
    P  I  V  G  N  L  L  K  S  L  L  G  K  +

241 GAATTGGAAATCATCTGATGTGGAATATCATTTAGCTAAATGAGCAACAGATGTCTTATT

301 TAAAAAAATAAATATGTTCCATC
```

Clone Rt-6

```
1   GCTTTGTAGGATAGACCTGCACTGAAGTCTTCCAGCCGTCTACATTCTGAGCACCAACTG

61  AACTACCCGAGCCCAAAGATGTTCACCTTGAAGAAATCCCTGTTACTCCTCTTTTTCCTT
                      M  F  T  L  K  K  S  L  L  L  L  F  F  L

121 GGGACCATCAACTTATCTCTCTGTGAGGAAGAGAGAAATGCAGAAGAAGAAAGAAGAGAT
    G  T  I  N  L  S  L  C  E  E  E  R  N  A  E  E  E  R  R  D
```

```
-continued
181 GAACCAGATGAAAGGGATGTTCAAGTGGAAAAACGACTTTCACCAAACCTGCTCAAGAGC
     E  P  D  E  R  D  V  Q  V  E  K  R  L  S  P  N  L  L  K  S 241 TTGTTGGGAAAATAACCAAAAATGTTAAGAATGGAATTGGAAATCATCTGATGTGAATA
     L  L  G  K  +

301 TCATTTAGCTAAATGCGCAACAGATGTCTTATTTAAAAAATAAATATGTTGCATAC
```

Clone Rt-17                                                    [SEQ ID NOS:18—19]
```
1    CCCCTCCAGCGTCTACATTCTCATAACCAACTGAACCACCCGAGCCCAAAGATGTTCAC
                                                          M  F  T 61   CTTGAAGAAATCCCTCTTACTCCTTTTCTTCCTTGGGACCATCAACTTATCTCTCTGTGA
      L  K  K  S  L  L  L  F  F  L  G  T  I  N  L  S  L  C  E 121  GGAAGAGAGATGCCGATGAAGAAAGAAGAGATGATCTCGAAGAAGGGATGTTGAAGT
       E  E  R  D  A  D  E  E  R  R  D  D  L  E  E  R  D  V  E  V 181  GGAAAAGCGATTTTTTCCAGTGATTGGAAGGATACTCAATGGTATTTTGGGAAAATAACC
       E  K  R  F  F  P  V  I  G  R  I  L  N  G  I  L  G  K  +

241  AAAAAAAGTTAAACTTGGAAATGGAATTGGAAATCATCTAATGTGGAATGTCATTTAG

301  CTAAATGCACATCAAATGTCTTATAAAAA
```

---

What is claimed is:

1. A polypeptide selected from the following peptides SEQ ID NOS: 1–11:
   F L P L I G R V L S G I L - amide,
   L L P I V G N L L K S L L - amide,
   L L P I L G N L L N G L L - amide,
   L L P I V G N L L N S L L - amide,
   V L P I I G N L L N S L L - amide,
   F L P L I G K V L S G I L - amide,
   F F P V I G R I L N G I L - amide,
   L S P N L L K S L L - amide,
   L L P N L L K S L L - amide,
   F V Q W F S K F L G R I L - amide, and
   G L L S G L K K V G K H V A K N V A V S L M D S L K C K I S G D C,
   and pharmaceutically acceptable salts of the peptides of SEQ ID NOS 1–11.

2. A therapeutic composition comprising one or more polypeptides according to claim 1, wherein the composition has antibacterial or antifungal activity.

3. An antimicrobial composition comprising one or more polypeptides according to claim 1, wherein the composition has antibacterial or antifungal activity.

4. The antimicrobial composition according to claim 3, wherein the composition has antibacterial or antifungal activity.

5. A medicament comprising one or more polypeptides according to claim 1, wherein the medicament has antimicrobial activity.

6. The medicament of claim 5, wherein said medicament further has antibacterial or antifungal activity.

7. A pharmaceutical composition comprising as an active ingredient one or more polypeptides according to claim 1 in an amount effective to inhibit microbial growth together with a pharmaceutically acceptable carrier or diluent.

8. A pharmaceutical composition according to claim 7, wherein said active ingredient is in an amount effective to inhibit bacterial or fungal activity.

9. A pharmaceutical composition according to claim 7, wherein said pharmaceutical composition is in a form for oral, intravenous, intramuscular or subcutaneous administration.

10. An isolated cDNA clone comprising the nucleic acid encoding the polypeptide sequence selected from the group consisting of SEQ ID NO: 2, 7, and 8.

11. A method for inhibiting microbial growth in animals, comprising the step of administering to an animal subject to a disorder caused by a microbial infection one or more polypeptides according to claim 1 in an antimicrobial effective amount.

12. A method for inhibiting bacterial or fungal growth in animals, comprising the step of administering to an animal subject to a disorder caused by bacterial or fungal infection one or more polypeptides according to claim 1 in an antimicrobial or antifungal effective amount.

13. A pharmaceutical composition according to claim 8, wherein said pharmaceutical composition is in a form for oral, intravenous, intramuscular or subcutaneous administration.

14. A method of inhibiting microbial growth in animals, comprising the step of administering to an animal subject suffering from a disorder caused by a microbial infection the pharmaceutical composition according to claim 7 in an antimicrobial effective amount.

15. A method according to claim 14, wherein the microbial growth is bacterial or fungal growth.

16. A method according to claim 14, wherein administering the pharmaceutical composition comprises injecting the pharmaceutical composition in a suitable amount to inhibit microbial growth.

17. A method according to claim 15, wherein administering the pharmaceutical composition comprises injecting the pharmaceutical composition in a suitable amount to inhibit bacterial or fungal growth.

* * * * *

SEQUENCE LISTING

<160> NUMBER OF SEQ ID NOS: 19

<210> SEQ ID NO: 1
<211> LENGTH: 13
<212> TYPE: PRT
<213> ORGANISM: Rana Temporaria

<400> SEQUENCE: 1

Phe Leu Pro Leu Ile Gly Arg Val Leu Ser Gly Ile Leu
 1               5                  10

<210> SEQ ID NO: 2
<211> LENGTH: 13
<212> TYPE: PRT
<213> ORGANISM: Rana Temporaria

<400> SEQUENCE: 2

Leu Leu Pro Ile Val Gly Asn Leu Leu Lys Ser Leu Leu
 1               5                  10

<210> SEQ ID NO: 3
<211> LENGTH: 13
<212> TYPE: PRT
<213> ORGANISM: Rana Temporaria

<400> SEQUENCE: 3

Leu Leu Pro Ile Leu Gly Asn Leu Leu Asn Gly Leu Leu
 1               5                  10

<210> SEQ ID NO: 4
<211> LENGTH: 13
<212> TYPE: PRT
<213> ORGANISM: Rana Temporaria

<400> SEQUENCE: 4

Leu Leu Pro Ile Val Gly Asn Leu Leu Asn Ser Leu Leu
 1               5                  10

<210> SEQ ID NO: 5
<211> LENGTH: 13

```
<212> TYPE: PRT
<213> ORGANISM: Rana Temporaria

<400> SEQUENCE: 5

Val Leu Pro Ile Ile Gly Asn Leu Leu Asn Ser Leu Leu
 1               5                  10

<210> SEQ ID NO: 6
<211> LENGTH: 13
<212> TYPE: PRT
<213> ORGANISM: Rana Temporaria

<400> SEQUENCE: 6

Phe Leu Pro Leu Ile Gly Lys Val Leu Ser Gly Ile Leu
 1               5                  10

<210> SEQ ID NO: 7
<211> LENGTH: 13
<212> TYPE: PRT
<213> ORGANISM: Rana Temporaria

<400> SEQUENCE: 7

Phe Phe Pro Val Ile Gly Arg Ile Leu Asn Gly Ile Leu
 1               5                  10

<210> SEQ ID NO: 8
<211> LENGTH: 10
<212> TYPE: PRT
<213> ORGANISM: Rana Temporaria

<400> SEQUENCE: 8

Leu Ser Pro Asn Leu Leu Lys Ser Leu Leu
 1               5                  10

<210> SEQ ID NO: 9
<211> LENGTH: 10
<212> TYPE: PRT
<213> ORGANISM: Rana Temporaria

<400> SEQUENCE: 9

Leu Leu Pro Asn Leu Leu Lys Ser Leu Leu
 1               5                  10

<210> SEQ ID NO: 10
<211> LENGTH: 13
<212> TYPE: PRT
<213> ORGANISM: Rana Temporaria

<400> SEQUENCE: 10

Phe Val Gln Trp Phe Ser Lys Phe Leu Gly Arg Ile Leu
 1               5                  10

<210> SEQ ID NO: 11
<211> LENGTH: 33
<212> TYPE: PRT
<213> ORGANISM: Rana Temporaria

<400> SEQUENCE: 11

Gly Leu Leu Ser Gly Leu Lys Lys Val Gly Lys His Val Ala Lys Asn
 1               5                  10                  15

Val Ala Val Ser Leu Met Asp Ser Leu Lys Cys Lys Ile Ser Gly Asp
                20                  25                  30

Cys
```

-continued

```
<210> SEQ ID NO: 12
<211> LENGTH: 22
<212> TYPE: PRT
<213> ORGANISM: Rana Temporaria

<400> SEQUENCE: 12

Phe Ile Gly Ser Ala Leu Lys Val Leu Ala Gly Val Leu Pro Ser Val
 1               5                  10                  15

Ile Ser Trp Val Lys Gln
            20

<210> SEQ ID NO: 13
<211> LENGTH: 26
<212> TYPE: PRT
<213> ORGANISM: anitmicrobially active polypeptide

<400> SEQUENCE: 13

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
            20                  25

<210> SEQ ID NO: 14
<211> LENGTH: 323
<212> TYPE: DNA
<213> ORGANISM: Rana Temporaria
<220> FEATURE:
<221> NAME/KEY: CDS
<222> LOCATION: (37)..(219)

<400> SEQUENCE: 14
acaattctga gccaactgaa ccacccgagc ccaaag atg ttc acc ttg aag aaa          54
                                        Met Phe Thr Leu Lys Lys
                                         1               5 tcc ctg tta ctc ctc ttt ttc ctt ggg acc atc aac tta tct ctc tgt        102
Ser Leu Leu Leu Leu Phe Phe Leu Gly Thr Ile Asn Leu Ser Leu Cys
            10                  15                  20 gag gaa gag aga aat gca gaa gaa gaa aga aga gat gaa cca gat gaa        150
Glu Glu Glu Arg Asn Ala Glu Glu Glu Arg Arg Asp Glu Pro Asp Glu
        25                  30                  35 agg gat gtt caa gtg gaa aaa cga ctt tta cca att gtt gga aac ctg        198
Arg Asp Val Gln Val Glu Lys Arg Leu Leu Pro Ile Val Gly Asn Leu
    40                  45                  50 ctc aag agc ttg ttg gga aaa taaccaaaaa tgttaagaat ggaattggaa           249
Leu Lys Ser Leu Leu Gly Lys
 55                  60 atcatctgat gtggaatatc atttagctaa atgagcaaca gatgtcttat ttaaaaaaat      309
aaatatgttc catc                                                        323

<210> SEQ ID NO: 15
<211> LENGTH: 61
<212> TYPE: PRT
<213> ORGANISM: Rana Temporaria

<400> SEQUENCE: 15

Met Phe Thr Leu Lys Lys Ser Leu Leu Leu Leu Phe Phe Leu Gly Thr
 1               5                  10                  15

Ile Asn Leu Ser Leu Cys Glu Glu Glu Arg Asn Ala Glu Glu Glu Arg
            20                  25                  30

Arg Asp Glu Pro Asp Glu Arg Asp Val Gln Val Glu Lys Arg Leu Leu
        35                  40                  45
```

```
Pro Ile Val Gly Asn Leu Leu Lys Ser Leu Leu Gly Lys
         50                  55                  60

<210> SEQ ID NO: 16
<211> LENGTH: 356
<212> TYPE: DNA
<213> ORGANISM: Rana Temporaria
<220> FEATURE:
<221> NAME/KEY: CDS
<222> LOCATION: (79)..(252)

<400> SEQUENCE: 16
gctttgtagg atagacctgc actgaagtct tccagccgtc tacattctga gcaccaactg      60
aactacccga gcccaaag atg ttc acc ttg aag aaa tcc ctg tta ctc ctc       111
                   Met Phe Thr Leu Lys Lys Ser Leu Leu Leu Leu
                     1               5                  10 ttt ttc ctt ggg acc atc aac tta tct ctc tgt gag gaa gag aga aat      159
Phe Phe Leu Gly Thr Ile Asn Leu Ser Leu Cys Glu Glu Glu Arg Asn
             15                  20                  25 gca gaa gaa gaa aga aga gat gaa cca gat gaa agg gat gtt caa gtg      207
Ala Glu Glu Glu Arg Arg Asp Glu Pro Asp Glu Arg Asp Val Gln Val
         30                  35                  40 gaa aaa cga ctt tca cca aac ctg ctc aag agc ttg ttg gga aaa          252
Glu Lys Arg Leu Ser Pro Asn Leu Leu Lys Ser Leu Leu Gly Lys
 45                  50                  55 taaccaaaaa tgttaagaat ggaattggaa atcatctgat gtggaatatc atttagctaa    312
atgcgcaaca gatgtcttat ttaaaaaata aatatgttgc atac                      356

<210> SEQ ID NO: 17
<211> LENGTH: 58
<212> TYPE: PRT
<213> ORGANISM: Rana Temporaria

<400> SEQUENCE: 17

Met Phe Thr Leu Lys Lys Ser Leu Leu Leu Leu Phe Phe Leu Gly Thr
 1               5                  10                  15

Ile Asn Leu Ser Leu Cys Glu Glu Glu Arg Asn Ala Glu Glu Glu Arg
             20                  25                  30

Arg Asp Glu Pro Asp Glu Arg Asp Val Gln Val Glu Lys Arg Leu Ser
         35                  40                  45

Pro Asn Leu Leu Lys Ser Leu Leu Gly Lys
     50                  55

<210> SEQ ID NO: 18
<211> LENGTH: 329
<212> TYPE: DNA
<213> ORGANISM: Rana Temporaria
<220> FEATURE:
<221> NAME/KEY: CDS
<222> LOCATION: (53)..(235)

<400> SEQUENCE: 18
cccctccagc tgtctacatt ctcataacca actgaaccac ccgagcccaa ag atg ttc    58
                                                         Met Phe
                                                           1 acc ttg aag aaa tcc ctc tta ctc ctt ttc ttc ctt ggg acc atc aac      106
Thr Leu Lys Lys Ser Leu Leu Leu Phe Phe Leu Gly Thr Ile Asn
         5                  10                  15 tta tct ctc tgt gag gaa gag aga gat gcc gat gaa gaa aga aga gat      154
Leu Ser Leu Cys Glu Glu Glu Arg Asp Ala Asp Glu Glu Arg Arg Asp
         20                  25                  30
```

-continued

```
gat ctc gaa gaa agg gat gtt gaa gtg gaa aag cga ttt ttt cca gtg     202
Asp Leu Glu Glu Arg Asp Val Glu Val Glu Lys Arg Phe Phe Pro Val
 35              40                  45                  50 att gga agg ata ctc aat ggt att ttg gga aaa taaccaaaaa aagttaaaac   255
Ile Gly Arg Ile Leu Asn Gly Ile Leu Gly Lys
                55                  60 tttggaaatg gaattggaaa tcatctaatg tggaatgtca tttagctaaa tgcacatcaa   315
atgtcttata aaaa                                                    329
```

<210> SEQ ID NO: 19
<211> LENGTH: 61
<212> TYPE: PRT
<213> ORGANISM: Rana Temporaria

<400> SEQUENCE: 19

```
Met Phe Thr Leu Lys Lys Ser Leu Leu Leu Phe Phe Leu Gly Thr
 1               5                  10                  15

Ile Asn Leu Ser Leu Cys Glu Glu Glu Arg Asp Ala Asp Glu Glu Arg
                20                  25                  30

Arg Asp Asp Leu Glu Glu Arg Asp Val Glu Val Glu Lys Arg Phe Phe
            35                  40                  45

Pro Val Ile Gly Arg Ile Leu Asn Gly Ile Leu Gly Lys
 50                  55                  60
```